US00PP30637P2

(12) United States Plant Patent
Winslow

(10) Patent No.: US PP30,637 P2
(45) Date of Patent: Jul. 2, 2019

(54) ***IPOMOEA* PLANT NAMED 'BALSPOTBART'**

(50) Latin Name: *Ipomoea batatas*
Varietal Denomination: Balspotbart

(71) Applicant: Ball Horticultural Company, West Chicago, IL (US)

(72) Inventor: Benjamin K. Winslow, Austin, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/932,585

(22) Filed: Mar. 16, 2018

(51) Int. Cl.
*A01H 5/02* (2018.01)
*A01H 6/00* (2018.01)

(52) U.S. Cl.
USPC ..... Plt./258

(58) Field of Classification Search
USPC ..... Plt./258
CPC ... A01H 5/12; A01H 5/06; A01H 5/02; A01H 5/00; A01H 5/04; A01H 6/00
See application file for complete search history.

*Primary Examiner* — June Hwu
(74) *Attorney, Agent, or Firm* — Audrey Charles

(57) ABSTRACT

A new and distinct cultivar of an ornamental *Ipomoea* plant named 'Balspotbart', characterized by heart-shaped, dark purple-colored foliage, and moderately vigorous, compact, mounded-spreading growth habit, is disclosed.

1 Drawing Sheet

Latin name of genus and species of plant claimed: *Ipomoea batatas*.

Variety denomination: 'Balspotbart'.

BACKGROUND OF THE INVENTION

The present invention relates to a new and distinct cultivar of *Ipomoea* plant botanically known as *Ipomoea batatas* and hereinafter referred to by the cultivar name 'Balspotbart'.

The new cultivar originated in a controlled breeding program in Arroyo Grande, Calif. during October 2014. The objective of the breeding program was the development of ornamental *Ipomoea* cultivars with heart-shaped leaves, and a well-branched, mounded growth habit with good garden performance under high night temperatures.

The new ornamental *Ipomoea* cultivar is the result of cross-pollination. The female (seed) parent of the new cultivar is 'Venetian Mask', unpatented, characterized by its dark purple-colored foliage and vigorous, mounded-spreading growth habit. The male (pollen) parent of the new cultivar is 'Sweet Caroline Sweetheart Purple', U.S. Plant Pat. No. 18,573, characterized by its small to medium-sized, heart-shaped to spade-shaped dark purple-colored foliage and compact to moderately compact, mounded-spreading growth habit. The new cultivar was discovered and selected as a single plant within the progeny of the above stated cross-pollination during April 2015 in a controlled environment in Arroyo Grande, Calif.

Asexual reproduction of the new cultivar by terminal stem cuttings since April 2015 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balspotbart' as a new and distinct cultivar of *Ipomoea* plant:

1. Heart-shaped, dark purple-colored foliage; and
2. Moderately vigorous, compact, mounded-spreading growth habit.

Plants of the new cultivar differ from plants of the female parent primarily in having reduced growth vigor and a more compact, especially under high night temperatures, and more mounded growth habit. Plants of the new cultivar differ from plants of the male parent primarily in having a slightly greener mature upper surface foliage color with greyed-red venation and in having a more compact, especially under high night temperatures, and more mounded growth habit.

Of the many commercially available ornamental *Ipomoea* cultivars, the most similar in comparison to the new cultivar is Spotlight Black, 'Balspotack', U.S. Plant Pat. No. 28,555. However, in comparison, plants of the new cultivar differ from plants of 'Balspotack' in at least the following characteristics:

1. Plants of the new cultivar have heart-shaped foliage unlike plants of 'Balspotack';
2. Plants of the new cultivar have smaller leaves than plants of 'Balspotack'; and
3. Plants of the new cultivar have a slightly different foliage color than plants of 'Balspotack'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balspotbart'. The plants were grown in 4-inch pots for 9 weeks in a greenhouse in West Chicago, Ill.

DETAILED BOTANICAL DESCRIPTION

Figure 1:
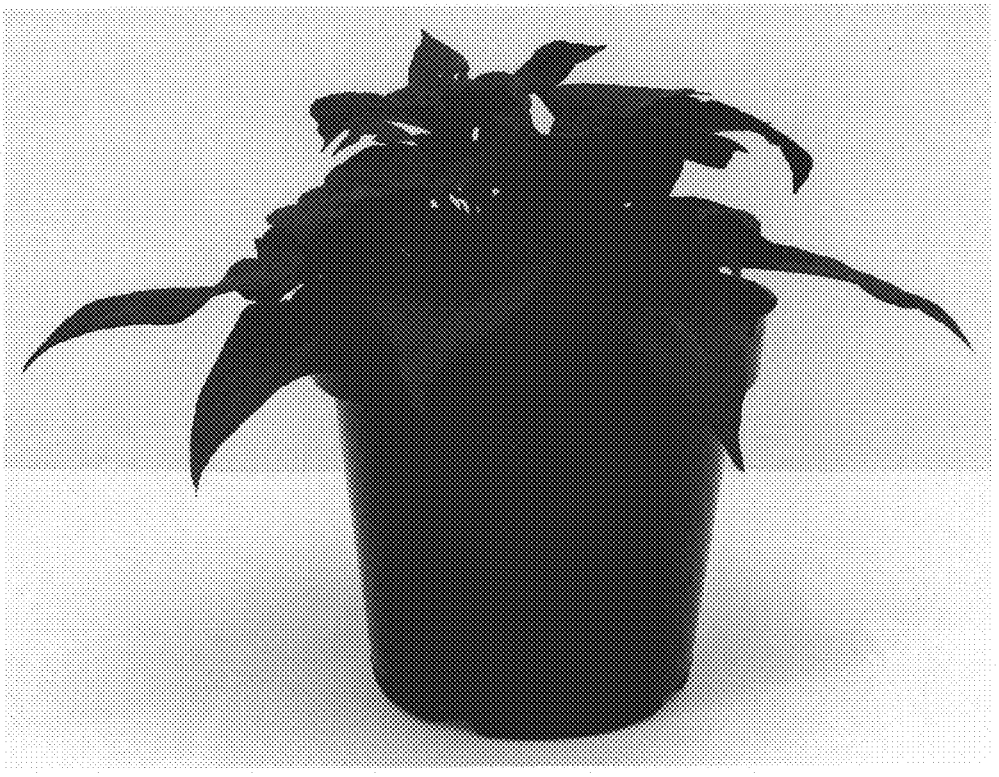
FIG. 1 illustrates a side view of the overall growth and habit of 'Balspotbart'.
Figure 2:
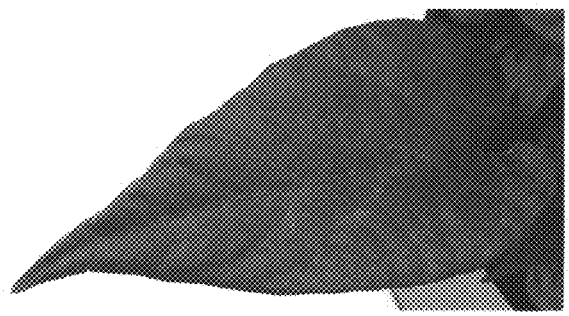
FIG. 2 illustrates a close-up view of an individual leaf of 'Balspotbart'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2018 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 10 weeks in a greenhouse utilizing a soilless growth medium. Greenhouse temperatures were maintained at approximately 68° F. to 72° F. (20° C. to 22° C.) during the day and approximately 64° F. to 66° F. (18° C. to 19° C.) during the night. Supplemental lighting was used. Measurements and numerical values represent averages of typical plants.

Botanical classification: *Ipomoea batatas* 'Balspotbart'.

Parentage:

*Female parent.*—'Venetian Mask', unpatented.

*Male parent.*—'Sweet Caroline Sweetheart Purple', U.S. Plant Pat. No. 18,573.

Propagation:

*Type cutting.*—Terminal stem.

*Time to initiate roots.*—Approximately 3 to 4 days.

*Time to produce a rooted cutting.*—Approximately 21 to 28 days.

*Root description.*—Fibrous, medium thickness, white to light brown in color.

*Rooting habit.*—Freely branching.

*Tuber description.*—Not available, tuber formation not observed to date.

Plant description:

*Commercial crop time.*—Approximately 4 to 5 weeks from a rooted cutting to finish in a 10 cm pot.

*Growth habit and general appearance.*—Moderately vigorous, compact, mounded-spreading growth habit.

*Size.*—Height: Approximately 10.0 cm. Width: Approximately 22.0 cm.

*Branching habit.*—Freely branching, pinching enhances basal branching. Quantity of main lateral branches per plant: Approximately 12.

*Branch.*—Shape: Round. Strength: Strong, slightly flexible. Length: Approximately 6.0 cm. Diameter: Approximately 4.0 mm. Length of central internode: Approximately 5.0 mm. Texture: Glabrous. Color of young stems: 145A with an overlay of N186D. Color of mature stems: N186D.

Foliage description:

*General description.*—Quantity of leaves per branch: Approximately 8. Fragrance: None detected. Form: Simple. Arrangement: Alternate, spiral.

*Leaves.*—Shape: Cordate. Margin: Entire. Apex: Broadly acuminate to broadly acute. Base: Cordate. Venation pattern: Palmate. Length of mature leaf: Approximately 8.0 cm. Width of mature leaf: Approximately 5.5 cm. Texture of upper and lower surfaces: Glabrous. Color of upper surface of young foliage: 144A with an overlay of N186C, venation of 187A to same color as lamina. Color of lower surface of young foliage: Closest to 146C with an overlay of N186C, venation of 146D. Color of upper surface of mature foliage: Closest to NN137A with a heavy overlay of N186A and venation of 187A. Color of lower surface of mature foliage: Closest to N186C, venation of N186D.

*Petiole.*—Length: Approximately 6.0 cm. Diameter: Approximately 2.0 mm. Texture: Glabrous. Color: 187B.

Flowering description: Not available, flower and seed formation not observed to date. The new ornamental *Ipomoea* cultivar is grown as a foliage plant and is not grown under conditions that are conducive to flower production.

Disease and pest resistance: Resistance to pathogens and pests common to *Ipomoea* has not been observed.

What is claimed is:

1. A new and distinct cultivar of an ornamental *Ipomoea* plant named 'Balspotbart', substantially as herein illustrated and described.

* * * * *